United States Patent [19]

Bülow et al.

[11] Patent Number: 5,452,618
[45] Date of Patent: Sep. 26, 1995

[54] MECHANISM FOR OSCILLATING A SAMPLE HOLDER WITHIN A SAMPLE VESSEL

[75] Inventors: Martin Bülow, Basking Ridge; André Micke, Summit, both of N.J.

[73] Assignee: The BOC Group, Inc., New Providence, N.J.

[21] Appl. No.: 311,077

[22] Filed: Sep. 23, 1994

[51] Int. Cl.⁶ ............................... G01N 1/10; G01N 1/16
[52] U.S. Cl. ..................................... 73/863.82; 73/863.85
[58] Field of Search .......................... 73/863.82, 863.85

[56] References Cited

U.S. PATENT DOCUMENTS

| | | | |
|---|---|---|---|
| 2,353,530 | 7/1944 | Walker | 73/863.85 X |
| 2,675,706 | 4/1954 | Edgar | 73/863.82 X |
| 3,121,334 | 2/1964 | Butt | 73/863.82 |
| 3,229,526 | 1/1966 | Kennedy | 73/863.82 X |
| 3,849,070 | 11/1974 | Garza et al. | 73/863.85 X |
| 4,054,060 | 10/1977 | Ueno et al. | 73/863.85 |
| 4,375,170 | 3/1983 | Sperry, III et al. | 73/863.85 |
| 4,499,776 | 2/1985 | Robinson | 73/863.85 |
| 5,049,492 | 9/1991 | Sauer et al. | 73/863.85 X |
| 5,296,197 | 3/1994 | Newberg et al. | 73/863.82 X |

*Primary Examiner*—Thomas P. Noland
*Attorney, Agent, or Firm*—David M. Rosenblum; Larry R. Cassett

[57] ABSTRACT

A mechanism used in connection with determining a time resolved interaction between a target substance, for instance, an adsorbent and at least one agent, for instance, an adsorbate capable of interacting with the target substance. In accordance with the method the target substance and agent(s) are introduced into a sample vessel. At the same time, the target substance is oscillated within the sample vessel without changing the volume of the sample vessel. A concentration of one or more components associated with the time resolved interaction as a function of time is measured by measuring chamber pressure and simultaneously performing a mass spectroscopical analysis of chamber content at discrete time intervals. The target substance is oscillated by a mechanical movement which oscillates a sample holder configured to hold the target substance. The movement has a finger-like member, preferably formed by welded steel bellows and a curved member rotating within the finger-like member so that motion of the finger-like member does not change chamber volume and therefore effect the pressure measurements that are to be made in accordance with the method.

9 Claims, 2 Drawing Sheets

MECHANISM FOR OSCILLATING A SAMPLE HOLDER WITHIN A SAMPLE VESSEL

BACKGROUND OF THE INVENTION

The present invention relates to a mechanism to be used in connection with a sample vessel in which a target substance is exposed to one or more agents in order to determine the time resolved interaction between the target substance and agent(s). More particularly the present invention relates to such a mechanism having an oscillatory movement for oscillating a sample holder within the sample vessel without changing volume of the sample vessel. Even more particularly, the present invention relates to such a mechanism in which a finger-like member, formed by a welded steel bellows, projects into the sample vessel and is attachable to the sample holder and in which the oscillatory movement acts upon the welded steel bellows and therefore the sample holder.

Detailed knowledge of the time resolved interaction between substances is important in determining the most proper and efficient industrial utilization of such substances. For instance, a complete understanding of the preferential adsorption characteristics of an adsorbent (a target substance) is critical for the practical utilization of the adsorbent in an industrial process involving the adsorption of a multicomponent, e.g. a binary mixture (containing two different agents) to be adsorbed by the adsorbent.

In case of adsorbents, the adsorption characteristics of an adsorbent may be determined through Fourier transform infrared techniques. The theory behind such methodology is that an adsorbent has active adsorbent centers that are infrared sensitive so that a spectrum can be determined that indicates the adsorption interaction with such active sites. The intensity of specfic bands of the spectrum is concentration dependent and thus, after calibration, one can quantitatively find the amount of the component that has ben adsorbed by the adsorbent. Measuring the amount of component within the adsorbent is a time dependent function. As a result, until equilibrium has been reached, the kinetics of adsorption of the adsorbent can be followed.

The disadvantage of Fourier transform infrared techniques is that they are only applicable to adsorbents that interact with adsorbates in an infrared sensitive spectra. Also, Fourier transform infrared techniques are only applicable at very high concentration steps. Thus, there exists classes of adsorbate/adsorbent interactions that cannot be followed through conventional techniques such as Fourier transform infrared techniques as well as interactions between adsorbates and adsorbents at very low concentration gradients.

Another method is to place the adsorbent into an sample vessel and to expose the adsorbent to agents capable of being adsorbed by the adsorbent. At the same time accurate pressure and composition measurements within the sample vessel have to be carried out. Advantages of such method include the lack of a requirement for interactions to be evidenced by infrared spectra and that the method is applicable at very low concentration steps. The technique involved in carrying out the method is discussed in Fundamentals of Adsorption, Proc. IVth Int. Conf. on Fundamentals of Adsorption, Kyoto, May 17–22, 1992, Hille et al., pp. 285–292 (1993). The problem with the technique is that, during its performance, a boundary layer can be rich in the agents interacting with the adsorbent forms which introduces errors into the measurements to be taken within the sample vessel.

As will be discussed, the present invention overcomes the difficulty involved in carrying out the aforementioned method by providing a movement for oscillating the sample holder to disrupt the boundary layer without changing volume of the sample vessel.

SUMMARY OF THE INVENTION

The present invention provides a mechanism for a sample holder configured to project into an access port of a sample vessel and to oscillate the sample holder within the sample vessel without effecting volume of the sample vessel. In accordance with such mechanism, a sealing means is provided for sealing the access port within the sample vessel. The sealing means has an opening. Also provided is a finger-like member having an open proximal end and a closed distal end and a means for connecting the sample holder to the distal end of the finger-like member. The finger-like member is sealably connected to the sealing means by its said open proximal end so that the open proximal end is aligned with the opening and the distal end is operable to project into the sample vessel when the mechanism is in use. A means projects into the finger-like member for imparting an oscillatory motion to the distal end of the finger-like member and therefore the sample holder without changing displacement of the finger-like member within the volume of the sample vessel. As a result, the volume of the sample vessel is not effected by the oscillatory motion of the distal end of the finger-like member.

It has been found by the inventors herein, as the adsorbate interacts with the adsorbent, a boundary layer forms on the adsorbent which influences the uptake rate of the particular mixture components on the adsorbent particles. As a result, pressure and concentration vs. time do not accurately reflect the distribution of components within the adsorbent particles. The oscillation of the sample holder and therefore the agent to interact with the target substance will disrupt this boundary layer and delete the influence of the latter on the uptake rate.

There are various engineering considerations that are involved in carrying out practical embodiments of the present invention. For instance, if an electrical motor were placed within the sample vessel, the sample vessel could become contaminated by lubricants used in the motor. The time resolved interaction between targets and agents could of course be affected by the electrical discharge produced by the motor. The problems involved in oscillating the sample holder are not solved by simply placing the motor outside the same vessel because a linkage to be oscillated must act on the sample holder while at the same time the sealed nature of the sample vessel must be maintained. The most important consideration is that the action of the linkage must not change the volume of the sample vessel. Since pressures are measured in fractions of millibars, even infinitesimal changes in the volume will effect the measurements.

As indicated above, the oscillatory linkage of the present invention is effectuated by a finger-like member having a distal end that is oscillated without changing displacement of the finger-like member. For instance, a vertical movement of the finger member, elongating and contracting such member would effect its displacement and therefore the volume of the sample vessel. Although side to side movements are possible, circular movements of the distal end of the finger-like member are preferred for the sake of the simplicity of mechanism and the ability to control the mechanism. As such, the term "oscillation" does not necessarily mean motion in only a single plane, in fact, as in the illustrated embodiment the oscillation inscribes a circular path. Additionally, although the present invention has ben described with referene to adsorption, such reference is for explanatory purposes only and does not constitute a limitation. For instance, target components and agents can be chamical reactants for which chemical reaction kinetics are to be determined.

BRIEF DESCRIPTION OF THE DRAWINGS

While the specification concludes with claims distinctly pointing out the subject matter that Applicants regard as their invention, it is believed that the invention will better understood when taken in connection with the accompanying drawings in which:

DETAILED DESCRIPTION

Figure 1:
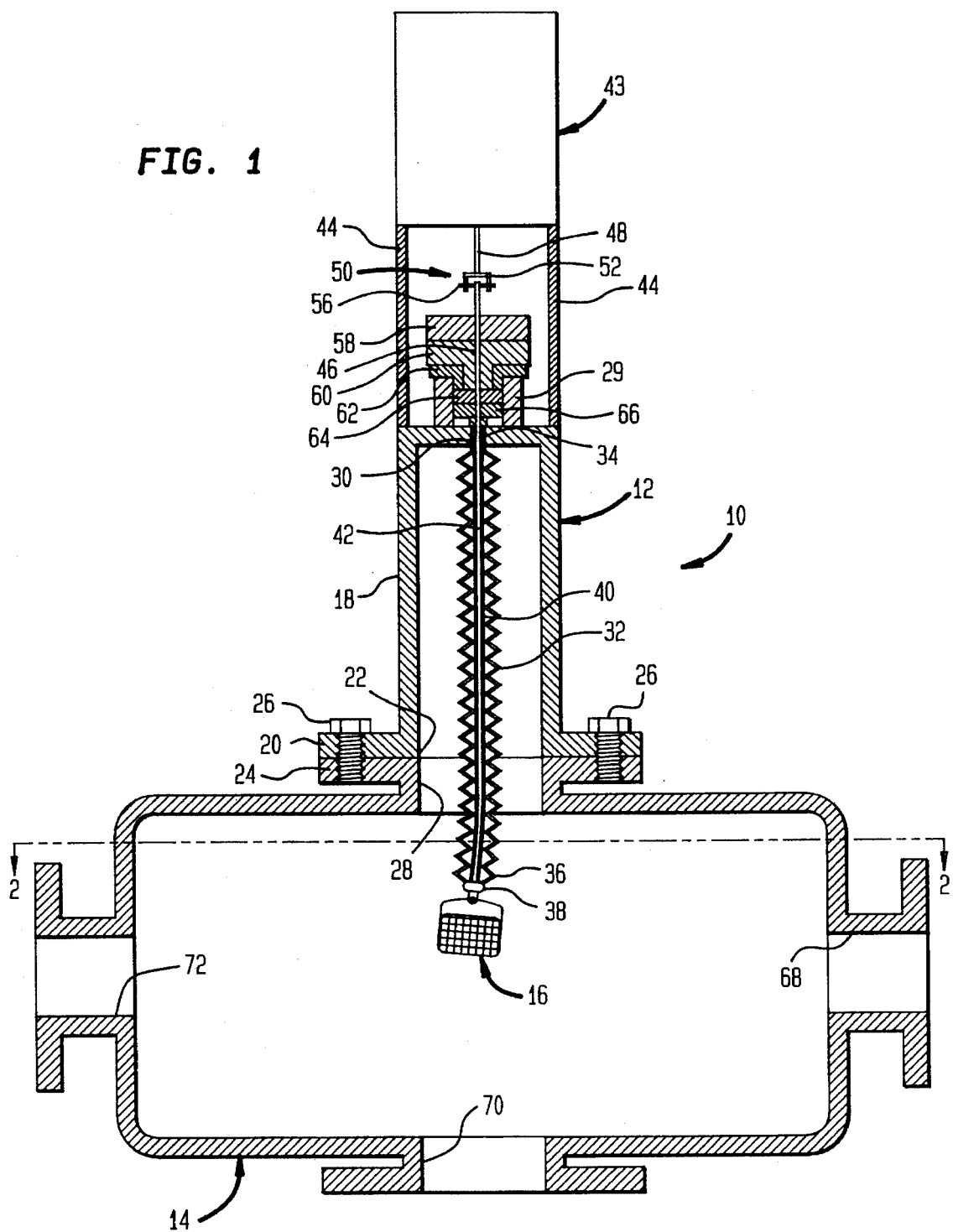
FIG. 1 is a sectional view of an apparatus for carrying out a method in accordance with the present invention.
Figure 2:
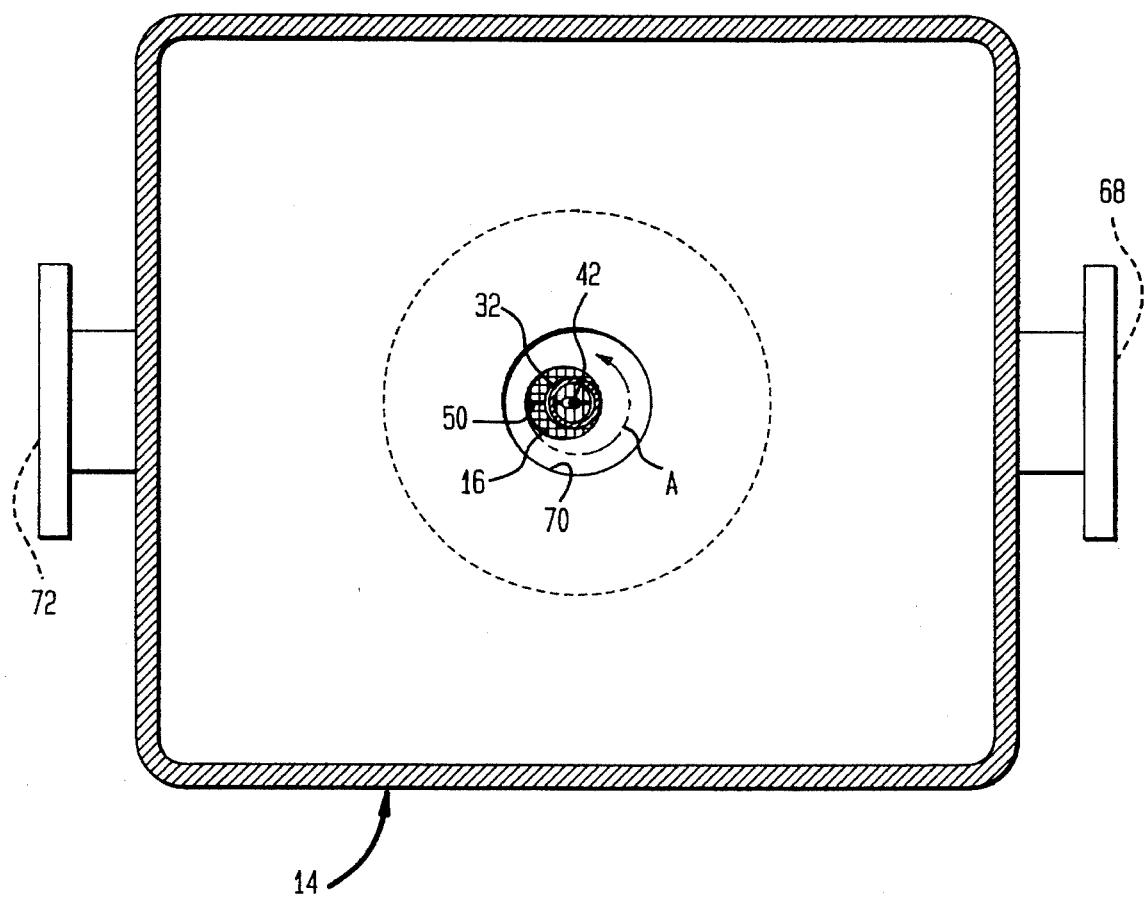
FIG. 2 is a sectional view of FIG. 1 taken along line 2—2 of FIG. 1.

With reference to the Figures a mechanism 10 in accordance with the present invention as illustrated. Mechanism 10 is provided with a movement 12 for oscillating a sample or a target substance to interact with one or more agents within a sample vessel 14. The sample is contained within a sample holder 16. Movement 12 has a base portion 18 which at one end is provided with a flange 20 surrounding an opening 22 of base portion 18. Flange 20 is designed to be connected to a complementary flange 24 of sample vessel 14 by bolts 26. Complementary flange 24 surrounds an access port 28 defined in sample vessel 14. In such manner, base portion 18 serves to seal access port 28 with its opening 22 aligned with access port 28.

Mechanical movement 12 is supported on a cylindrical crown piece 29 connected to base portion 18. Crown piece 29 is aligned with a top opening 30 of central portion 18.

Movement 12 utilizes a finger-like member 32, preferably a welded steel bellows, having an open proximal end 34 and a closed distal end 36. Attached to distal end 36 is a lug 38 which is used as a means to mount sample holder 16. Open proximal end 34 of finger-like member 32 is attached to base portion 18 with proximal end 34 aligned with top opening 30. In such manner, the seal between base portion 18 and sample vessel 14 is maintained by finger-like member 32. Located within finger-like member 32 is a sleeve 40 and an elongated member 42, formed from a wire, which can assume a curved shape. Elongated member 42 is rotated by an electrical motor 43 mounted to base portion 18 by posts 44. Rotation of elongated member 42 imparts a circular motion to closed distal end 36 of finger-like member 42. Finger-like member 42 does not itself rotate. However, the circular motion (Arrowhead A) of closed distal end 36 and therefore sample holder 16 will have orthogonal horizontal components so that sample holder 16 can said to be oscillated in a plane orthogonal to the rotation axis of movement 12. It will be understood that other mechanisms can impart the requisite circular motion to distal end 36 of finger-like member 42. For instance, a cam can be rotated within distal end 36 of finger-like member 42 within a horizontal plane to produce a circular motion of distal end 36.

Elongated member 42 is welded to a threaded member 46.

Threaded member 46 is connected to a shaft 48 of electrical motor 43 by a dog-like coupling 50 consisting of a slotted portion 52 connected to shaft 48. Threaded member 46 is provided with a shear pin 56 received within slotted portion 52 to transfer the rotation of shaft 48 to threaded member 46 and thus, elongated member 42.

Threaded onto threaded member 46 are a counter nut 58 which bears against a regulating screw 60 which in turn bears against a copper bearing 62. Copper bearing 62 is locked in place against regulating screw 60 by counter nuts 64 and 66. Adjusting regulating screw 60 will urge elongated member 42 downwardly against closed distal end 36 of finger-like member 32. The compression strain of elongated member 42 acting against shaft 48 of electrical motor 43 will cause elongated member 42 to assume a curved shape which will in turn curve finger-like member 32. Thus, the amount of curvature, within narrow limits, of member 42 can be adjusted to in turn adjust the period of oscillation of sample holder 16 for a given speed of electrical motor 43.

Since finger-like member 32 neither stretches nor contracts, its displacement remains constant and the volume within sample vessel 14 therefore also remains constant. Sample vessel 14 is also provided with access ports 68, 70 and 72. In a manner similar to that discussed above access port 68 is used to connect a manometer to sample vessel 14. Access port 70 is used to connect a source of agents that interact with the sample contained within sample holder 16. Access port 72 is used to connect a mass spectrometer to sample vessel 14 so that the concentration of the various components contained within sample vessel 14 can be continually tested.

While the present invention has been described with reference to a preferred embodiment, as will occur to those skilled in the art, numerous additions, omissions and changes can be made without departing from the spirit and scope of the present invention.

We claim:

1. A mechanism for a sample holder configured to project into an access port of a sample vessel and to oscillate a sample holder within said sample vessel without effecting volume of the sample vessel, said mechanism comprising:

sealing means for sealing said access port of said sample vessel;

said sealing means having an opening;

a finger-like member having an open proximal end and a closed distal end;

means for connecting said sample holder to said distal end of said finger-like member;

said finger-like member sealably connected to said sealing means by its said open proximal end so that said open proximal end is aligned with said opening and said distal end is operable to project into said sample vessel when said movement is in use; and means projecting into said finger-like member for imparting oscillatory motion to said distal end of said finger-like member and therefore said sample holder without changing displacement of said finger-like member, whereby the oscillatory motion of the finger-like member will not effect the volume of the sample vessel.

2. The mechanism of claim 1, wherein said access port has a flange and said sealing means comprises a complementary flange and a gasket configured to be sealable interposed between said complementary flange of said sealing means and said flange of said access port.

3. The mechanism of claim 1, wherein said finger-like member comprises a welded steel bellows.

4. The mechanism of claim 1, wherein said oscillatory motion means comprises:

a flexible elongated member forced against said distal end of said finger-like member from inside said finger-like member by a compressive force so that said wire assumes a curved form; and a shaft connected to said flexible elongated member for imparting rotary movement to said flexible elongated member and therefore eccentric movement to said distal end of said finger-like member with respect to said rotary movement; and a motor coupled to said shaft for imparting said rotary movement to said shaft.

5. The mechanism of claim 4, wherein said finger-like member comprises a welded steel bellows.

6. The mechanism of claim 5, wherein said access port has a flange and said sealing means comprises a complementary flange and a gasket configured to be sealable interposed between said complementary flange of said sealing means and said flange of said access port.

7. The mechanism of claim 6, further comprising means for adjusting said compressive force and therefore the curvature of said flexible elongated member.

8. The mechanism of claim 7, wherein said motor comprises an electric motor mounted on said complementary flange of said sealing means.

9. The mechanism of claim 4, further comprising means for adjusting said compressive force and therefore the curvature of said flexible elongated member.

* * * * *